United States Patent [19]

Buckler et al.

[11] Patent Number: 5,112,738
[45] Date of Patent: May 12, 1992

[54] HISTAMINE DERIVATIVES, IMMUNOGEN CONJUGATES AND ANTIBODIES RAISED THERETO

[75] Inventors: Robert T. Buckler, Edwardsburg, Mich.; Frank A. Dailey, Veradale; John A. Ficalora, Colbert, both of Wash.; John J. Gavin, Germantown, Md.; Gregory A. Plunkett, Spokane, Wash.

[73] Assignee: Miles Inc., Elkhart, Ind.

[21] Appl. No.: 266,227

[22] Filed: Oct. 28, 1988

Related U.S. Application Data

[63] Continuation of Ser. No. 752,320, Jul. 3, 1985, abandoned.

[51] Int. Cl.⁵ .............. G01N 33/535; C07K 15/28
[52] U.S. Cl. .................. 435/7.93; 435/240.27; 435/975; 436/518; 436/543; 436/548; 436/808; 436/822; 436/823; 530/363; 530/403; 530/807; 530/808; 530/809; 530/388.24; 530/388.9; 935/103; 935/110
[58] Field of Search .............. 436/822, 808, 823, 543, 436/518, 548; 530/807, 808, 809, 387, 363, 403; 435/240.27, 7, 810, 7.93, 975; 935/103, 110

[56] References Cited

U.S. PATENT DOCUMENTS

| | | | |
|---|---|---|---|
| 2,372,066 | 3/1945 | Fell | 424/88 |
| 3,822,245 | 7/1974 | Spector | 436/822 |
| 4,329,281 | 5/1982 | Christenson | 436/822 |
| 4,376,110 | 3/1983 | David | 436/548 |
| 4,521,510 | 6/1985 | Geltosky | 436/548 |
| 4,594,325 | 7/1986 | Lundak | 435/240 |
| 4,608,336 | 8/1986 | Benovic | 436/822 |
| 4,762,781 | 8/1988 | Geffard | 436/543 |

FOREIGN PATENT DOCUMENTS

| | | |
|---|---|---|
| 0116095 | 11/1942 | Austria . |
| 0447395 | 1/1972 | Austria . |
| 1341375 | 12/1973 | United Kingdom . |

OTHER PUBLICATIONS

Panula: Proc. Natl. Acad. Sci. (USA) 81 pp. 2572-2576, (1984).
Mita: Agents and Actions 14 (5/6), pp. 574-579, 1984.
Burtin-Laborde: Chemical Abstracts 74:123114a (1971).
Bieganski: Chemical Abstracts 104:144491z (1985)

*Primary Examiner*—Mary E. Ceperley
*Attorney, Agent, or Firm*—E. P. Gray; M. G. Boguslaski

[57] ABSTRACT

Histamine derivatives, immunogen conjugates comprising histamine or said histamine derivatives coupled to immunogenic carrier materials and antibodies prepared against such immunogen conjugates are disclosed. Such antibodies are useful in immunoassays for determining histamine release in biological fluids.

6 Claims, No Drawings

HISTAMINE DERIVATIVES, IMMUNOGEN CONJUGATES AND ANTIBODIES RAISED THERETO

This application is a continuation of U.S. Ser. No. 752.320, filed Jul. 03, 1985 now abandoned.

BACKGROUND OF THE INVENTION

Histamine is a powerful vasoactive mediator which is released from specifically sensitized tissue mast cells and basophils following exposure to specific allergens, thus triggering an allergic response in an individual. While in vivo diagnosis of an allergic reaction may be accomplished by an allergen skin test, such testing may be dangerous due to the possibility of an anaphylactic reaction, may sensitize the patient to the allergen and is generally uncomfortable. In vitro test methods are available for measuring the concentration of allergen-specific IgE antibody in serum. However it is believed that a more useful determination would be that of histamine release which may reflect more accurately the in vivo allergy response. Accordingly, the present invention provides histamine derivatives, immunogen conjugates comprising histamine or said histamine derivatives coupled to immunogenic carrier materials and antibodies prepared against such immunogen conjugates. Such antibodies are useful in immunoassays for determining the quantity of histamine in biological or laboratory fluids as, for example, following challenge of sensitized basophils with a battery of allergens.

DESCRIPTION OF PERTINENT ART

European Patent Application 110640 A2 discloses a receptor-based competitive inhibition assay for determining histamine levels in a body or laboratory fluid. Also disclosed are "histamine-indicator" conjugates such as histamine-horseradish peroxidase conjugate and histamine-alkaline phosphatase conjugate, the latter being conjugated to histamine by reaction with 1-ethyl-3-(3-dimethylaminopropyl) carbodiimide. The above-noted published patent application reviews various other methodologies for the quantitative determination of histamine such as variations of an ortho-phthalaldehyde conjugation assay, an enzymatic isotopic assay and chromatographic techniques.

In *Proc. Natl. Acad. Sci. USA*, Vol. 81, pp. 2572-2576 (April 1984) disclosed is the use of a histamine antiserum in an immunohistochemical study of histamine-containing cells in rat brain. Said study was undertaken to determine if histamine acts as a neurotransmitter in the mammalian central nervous system.

Mita et al (*Agents and Actions*, Vol 14, 5/6, 1984) disclose various hapten-carrier conjugates used in an attempt to raise a polyclonal antibody to histamine. However, the authors note that the attempt to raise a specific antibody to histamine was unsuccessful.

SUMMARY OF THE INVENTION

The present invention is directed to certain histamine derivatives selected from the group consisting of:

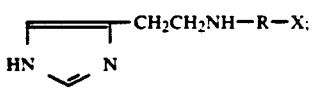

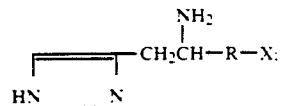

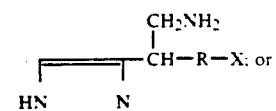

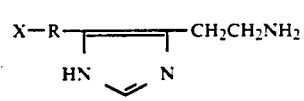

wherein R is a linking group and X is a terminal functional group selected from carboxyl, amino, thiol or hydroxyl.

Also disclosed are histamine immunogen conjugates of immunogenic carriers coupled to histamine derivatives or histamine, said conjugates selected from the group consisting of:

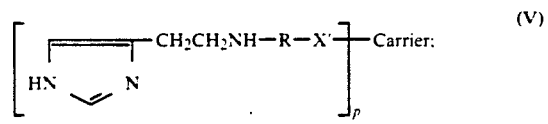

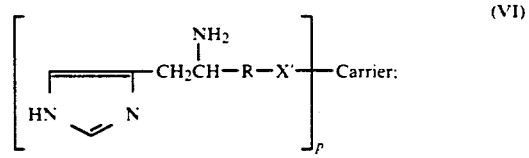

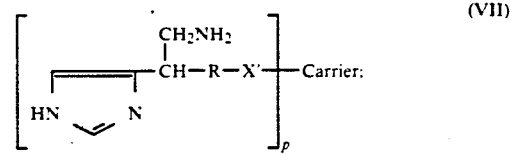

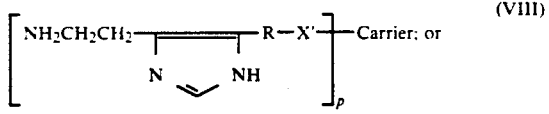

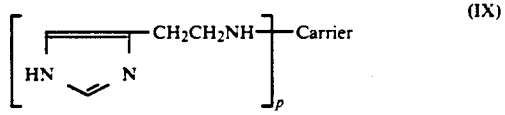

wherein R group, X' is the residue from terminal functional group X remaining after coupling said derivative to said immunogenic carrier through said linking group R, p is from about 1 to about 120 and Carrier is an immunogenic carrier material.

The invention is further directed to antibodies prepared against the above-described conjugates including monospecific (i.e., monoclonal) antibodies and the use thereof in test kits and immunological methods for determining histamine in biological or laboratory fluids.

DETAILED DESCRIPTION OF THE INVENTION

The histamine derivatives of the present invention may be prepared in such ways as to encompass a wide range of linking groups R and terminal functional groups X. For example, R may be linear or branched alkylenes comprising from 1 to as many as 15, more usually 10 or less, and normally less than 6 carbon atoms (i.e., methylene, ethylene, n-propylene, iso-propylene, n-butylene, and so forth). In addition, such alkylenes can contain other substituent groups such as cyano, amino (including substituted amino), acylamino, halogen, thiol, hydroxyl, carbonyl groups, carboxyl (including substituted carboxyls such as esters, amides, and substituted amides). The linking group R can also contain or consist of substituted or unsubstituted aryl, aralkyl, or heteroaryl groups (e.g., phenylene, phenethylene, and so forth). Additionally, such linkages can contain one or more heteroatoms selected from nitrogen, sulfur and oxygen in the form of ether, ester, amido, amino, thio ether, amidino, sulfone, or sulfoxide. Also, such linkages can include unsaturated groupings such as olefinic or acetylenic bonds, imino, or oximino groups. Preferably R will be a chain, usually aliphatic comprising between 1 and about 20 atoms, more usually between 1 and 10, excluding hydrogen, of which between 0 and 5 are heteroatoms selected from nitrogen, oxygen, and sulfur. Therefore, the choice of linking group R is not critical to the present invention and may be selected by one of ordinary skill taking normal precautions to assure that stable compounds are produced. Similarly, the terminal functional group X can vary widely, although amino, carboxyl, thiol and hydroxyl are preferred. Of the preferred derivatives, the following derivative is particularly preferred

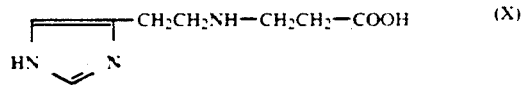

Representative methodologies for preparing the histamine derivatives having various linking groups R and terminal functional groups X will now be provided.

Histamine derivatives of formula I wherein X is carboxyl may be prepared by the reaction of histamine with omega-bromoalkanoic acids (i.e., Br—$CH_2$—$_n$—COOH, where n is about 1 to about 10). Those derivatives of formula I wherein X is amino can be synthesized by the reaction of histamine with omega-bromoalkylphthalimides to produce an intermediate of the formula

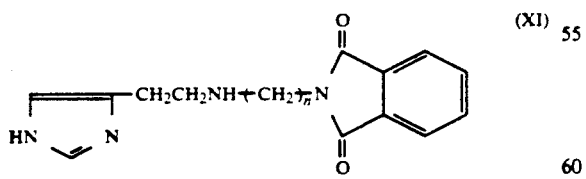

wherein n has a value of about 1 to about 10. Subsequent treatment of intermediate XI with hydrazine gives rise to the corresponding amino-functionalized histamine derivative of formula I (i.e., wherein R is $(CH_2)_n$ and X is amino).

Derivatives of formula I wherein X is thiol may be prepared by reacting the corresponding amino compound with N-succinimidyl-3-(2-pyridyldithio) propionate according to the method of J. Carlson, et al. *Biochem. J.*, 173, 723 (1978), which is, as well as all other references cited herein, incorporated by reference. Removal of the resulting protecting group yields the derivative of formula I having the formula

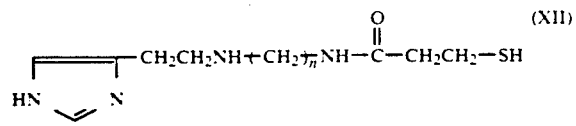

wherein n has a value of from about 1 to about 10. Alternatively, those derivatives of formula I wherein X is thiol may also be prepared by reacting the corresponding amino compound with SAMSA reagent as described by Klotz and Heiney, *Arch. Biochem. Biophys.*, 95, 605 (1964). Subsequent removal of the protecting group yields a derivative of formula I having the formula

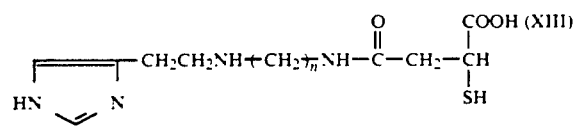

wherein n may be about 1 to about 10.

Histamine derivatives of formula I wherein X is hydroxyl may be readily prepared, for example, by the lithium aluminum hydride reduction of the corresponding carboxyl derivative, e.g.,

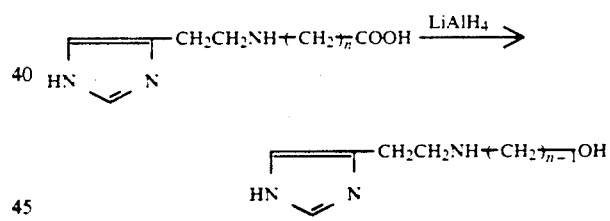

wherein n may be about 1 to about 10.

Histamine derivatives of formula II may be prepared, for example, by the chemical transformation of L-histidinol (Isn and Casy, *J. Med. Chem.*, 13, 1027, 1970) by the following representative reaction sequence:

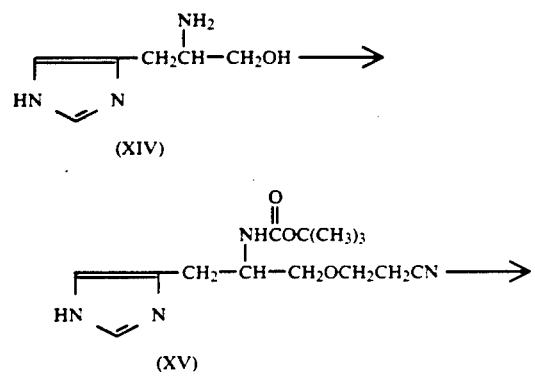

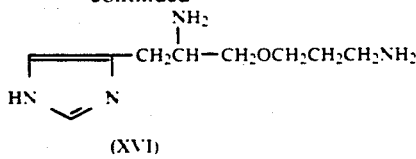

(XVI)

The amino functionality of L-histidinol (XIV) is protected as the t-boc derivative and the hydroxyl group reacted with acrylonitrile to give intermediate XV (R. T. Buckler and F. E. Ward, U.S. Pat. No. 4,495,281). Catalytic reduction of the cyano group followed by removal of the t-boc protecting group with dilute HCl renders compound XVI (i.e., a species of histamine derivatives of formula II wherein R is —CH$_2$OCH$_2$CH$_2$CH$_2$— and X is NH$_2$).

Functionalized histamine derivatives of formula III may, for example, be prepared from the N-triphenylmethyl (i.e., trityl) derivative of imidazole-4-acetonitrile, XVII, (J. I. DeGraw, et al, *J. Med. Chem.*, 20, 1671, 1977) by the following representative reaction sequence:

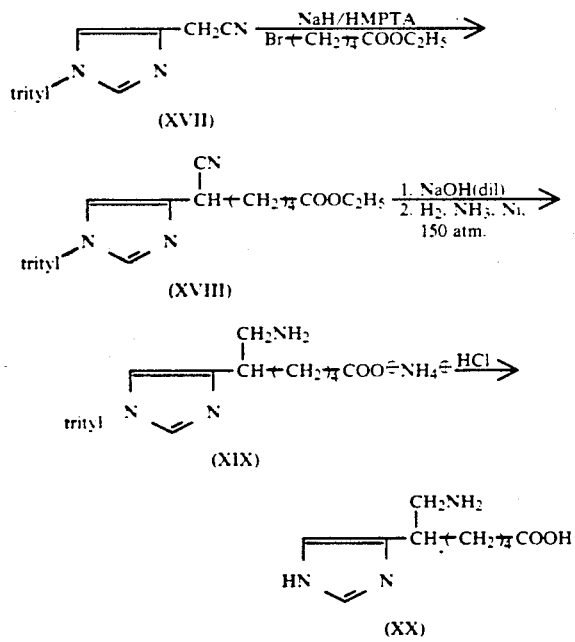

Compound XVII is alkylated with ethyl 5-bromovalerate (Aldrich Chemical Co., Milwaukee, Wis.) in the presence of sodium hydride and hexamethylphosphoric triamide (HMPTA). The product XVIII, after hydrolysis of the ester function with dilute alkali, is reduced to the intermediate XIX. A variety of conditions can be used for this reduction, such as by raney nickel-ammonia-hydrogen at 150 atmospheres pressure (e.g., G. J. Durant, et al, British Patent 1,341,376; *Chem Abs.*, 80P, 95958 g, 1974). Removal of the trityl protecting group renders XX, a histamine derivative of formula III wherein R is -(CH$_2$)$_4$ and X is carboxyl.

Representative histamine derivatives of formula IV may be prepared, for example, by the procedure described by L. K. Kesztyus, et al in British Patent 1,017,479 and *Chem. Abst.*, 64, P12470j. Said procedure would prepare a representative derivative of formula IV having the following formula:

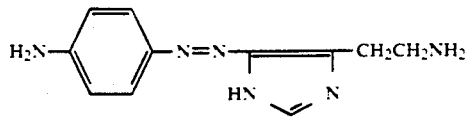

(XXI)

The histamine derivatives may then be used to couple said derivatives to an immunogenic carrier material through linking group R and terminal functional group X of the derivatives. The immunogenic carrier material can be selected from any of those conventionally known. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 5,000 and 10,000,000, preferably greater than 15,000 and more usually greater than 50,000. Generally, proteins taken from one animal species will be immunogenic when introduced into the blood stream of another species. Particularly useful proteins are those such as albumins, globulins, enzymes, hemocyanins, glutelins or proteins having significant non-proteinaceous constituents, e.g., glycoproteins, and the like. Further reference for the state-of-the-art concerning conventional immunogenic carrier materials and techniques for coupling haptens thereto may be had to the following: Parker, *Radioimmunoassay of Biologically Active Compounds,* Prentice-Hall (Englewood Cliffs, N.J., USA, 1976), Butler, *J. Immunol. Meth.* 7:1-24 (1975) and *Pharmacol. Rev.* 29(2):103-163 (1978); Weinryb and Shroff, *Drug Metab. Rev.* 10:P271-283 (1975); Broughton and Strong, *Clin. Chem.* 22:726-732 (1976); and Playfair et al., *Br. Med. Bull.* 30:24-31 (1974). Preferred immunogenic carrier materials for use in the present invention are bovine serum albumin and keyhole limpet hemocyanin. Particularly preferred for use in the present invention is keyhole limpet hemocyanin. Accordingly, a particularly preferred immunogen conjugate is that conjugate formed by coupling the histamine derivative of formula X to keyhole limpet hemocyanin.

The histamine derivatives are couplable to the immunogenic carrier materials according to well known techniques. For example, when the terminal functional group X of the histamine derivative is amino, said derivative can be attached directly to the carrier by the following means. The amino group of the histamine moiety can be attached to amino-containing carriers (e.g., protein or polypeptide carriers) by toluene-2,4-diisocyanate [A. F. Schick and S. J. Singer, *J. Biol. Chem.* 244:406 (1969)]; glutaraldehyde [L. A. Frohman, et al. *Endocrinol.* 87:1055 (1970)]; bis-imidates [A. Dutton et al., *Biochem. Biophys. Res. Comm.* 23:730 (1966)]; and chlorotriazine [T. Land et al., *J. C. S. Perkin* 4:2189 (1977)]. Also, said amino groups can be coupled to carboxyl-bearing carriers (e.g., again, protein or polypeptide carriers) by common peptide bond-forming reactions by means of mixed anhydrides, activated esters, acyl azide formation, carbodiimides and the like. See *Peptides*, ed. Goodman and Meinhofer, John Wiley & Sons (New York, 1977) p. 6 et seq, and *The Peptides, Analysis, Synthesis, Biology*, Vol. 1, Academic Press (New York, 1979). The same methods apply likewise for attaching carboxylated derivatives (i.e., those histamine derivatives wherein the terminal functional group X is carboxyl) to amino-bearing carriers.

Thiolated histamine derivatives (i.e., those histamine derivatives wherein the terminal functional group X is thiol) can be prepared from the corresponding amino compounds by the procedure of I. M. Klotz and R. E. Heiney, *Arch. Biochem. Biophys.* 95:605 (1962) and these attached to thiol-containing polymers (IgG or thiolated proteins) by the disulfide exchange procedure [J. Martin, et al., *Biochem.* 20:4229 (1981)]. Alternatively, an amino-containing polymer can be reacted with the reagent MBS and the product coupled to thiol-containing derivatives by the process described by T. Kitagawa and T. Aikawa, *J. Biochem.* 79:233 (1976). Various other coupling techniques are available to those of ordinary skill in the art for joining the various histamine derivatives of the present invention with conventional immunogenic carrier materials.

Residue X' of the conjugate will, of course, vary according to the terminal functional group X in the particular histamine derivative used, that is, may be imino, sulfo, oxy and the like.

Alternatively, the terminal amino group of the histamine molecule per se may be coupled directly to immunogenic carrier materials (for example bovine or human serum albumin, keyhole limpet hemocyanin and the like) without an intermediate linking group R or other terminal functional groups X as described previously for the histamine derivatives of the present invention. However, in forming these conjugates the basic character of the terminal amino group must be maintained in order to utilize a conjugate of this type (i.e., one not containing an intermediate linking group R or other terminal functional groups X) in the formation of antibodies having sufficient specificity for histamine without significant cross-reactivity with histidine. If however the basic character of this terminal amino function is lost during coupling, the conjugates of this type are still useful in various of the immunoassays as described, infra, for purposes other than raising antibodies thereto. The coupling for these conjugates may be carried out by conventional techniques such as described above as by common peptide bond-forming reactions by means of mixed anhydrides, activated esters, acyl azide formation, carbodiimides and the like. Preferably for these conjugates the coupling reagent is a carbodiimide, particularly 1-ethyl-3-(3-dimethylaminopropyl) carbodiimide hydrochloride (EDAC).

It should be pointed out that as used in the formulae describing the immunogen conjugates herein, "p" represents the number of histamine moieties conjugated to the carrier. The number p is sometimes referred to as the epitopic density of the immunogen and in the usual situation will be on the average from about 1 to about 120, more normally from 1 to about 50. These densities however may vary greatly depending on the particular carrier material used.

Preparation of specific antibodies using the present immunogen conjugates may follow any conventional technique. Numerous texts are available describing the fundamental aspects of inducing antibody formation; for example reference may be made to Parker, *Radioimmunoassay of Biologically Active Compounds*, Prentice-Hall (Englewood Cliffs, N.J., USA, 1976). In the usual case, a host animal such as a rabbit, goat, mouse, guinea pig or horse is injected at one or more of a variety of sites with the immunogen conjugate, often in admixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps may be taken to remove undesired material such as nonspecific antibodies before the antiserum is considered suitable for use in performing actual assays.

In a preferred embodiment the antibodies are obtained by somatic cell hybridization techniques, such antibodies being commonly referred to as monoclonal antibodies. Monoclonal antibody production will be exemplified in detail hereinafter, however, reviews of such monoclonal antibody techniques may be found in the following publications: *Lymphocyte Hybridomas*, ed. Melchers et al, Springer-Verlag (New York 1978); *Nature* 266:495 (1977); *Science* 208:692 (1980); and *Methods in Enzymology* 73 (Part B): 3–46 (1981).

The antibodies prepared from the immunogens of the present invention can be used in various immunoassay methods, and the corresponding reagent means, for determining histamine, including agglutination techniques, radioimmunoassays, heterogeneous enzyme immunoassays (e.g., U.S. Pat. No. 3,654,090), heterogeneous fluorescent immunoassays (e.g., U.S. Pat. Nos. 4,201,763; 4,171,311; 4,133,639 and 3,992,631), and homogeneous (separation-free) immunoassays. Such homogeneous immunoassays include techniques such as fluorescence quenching or enhancement (e.g., U.S. Pat. No. 4,160,016), fluorescence polarization (*J. Exp. Med.* 122:1029 (1965), enzyme substrate-labeled immunoassay (U.S. Pat. No. 4,279,992 and U.K. Pat. Spec. 1,552,607), prosthetic group-labeled immunoassay (U.S. Pat. No. 4,238,565), enzyme modulator-labeled immunoassay, e.g., using inhibitor labels (U.S. Pat. Nos. 4,134,792 and 4,273,866), enzyme-labeled immunoassay (e.g., U.S. Pat. No. 3,817,837), energy transfer immunoassay (U.S. Pat. No. 3,996,345), chemically-excited fluorescence immunoassay (U.S. Pat. No. 4,238,195) and double antibody steric hindrance immunoassay (U.S. Pat. Nos. 3,935,074 and 3,998,943). Moreover, derivatives of the present invention can be used to prepare the labeled conjugates needed to perform certain of the various immunoassays described above. Appropriate derivatives can be, for example, radio-labeled, labeled with fluorescent moieties, chemiluminescent moieties and the like in accordance with standard methods. Likewise the appropriate labeling moiety for homogeneous techniques, e.g., an enzyme substrate, a prosthetic group, an enzyme modulator, or an enzyme (which is a protein and can be coupled similarly to the immunogenic carrier as described above) can be coupled to the derivatives to yield labeled conjugates. In a preferred embodiment the histamine release immunoassay is carried out conveniently via an enzyme immunoassay wherein the antibody (preferably a monoclonal antibody) is coupled to an enzyme such as horseradish peroxidase, alkaline phosphatase, lysozyme, glucose-6-phosphate dehydrogenase and the like. The coupling is accomplished by conventional techniques using various cross-linking agents such as glutaraldehyde, dimaleimide or thiol reagents as described by J. W. Freytag, et al, *Clin. Chem.*, 30, 417–420 (1984). Enzyme substrate is then provided (such as a chromogenic enzyme substrate), and antigen concentration may be readily correlated to standard antigen concentrations.

Such assays are typically conducted on biological or laboratory fluids. The phrase "biological or laboratory fluids" as used herein refers to fluid preparations such as, for example, extracts prepared from a variety of biological substances such as cheese, fish, wine and the like as well as natural biological materials such as blood, urine, saliva and the like. The phrase also refers to any substance or material the histamine content of which is to be determined, including areas in the field of histochemistry where it may be desireable to determine the location of histamine in a given sample.

Also provided within the scope of the present invention is a test kit such as a mercantile unit in order to carry out an immunoassay for histamine. Such kits will include one or more containers such as microtiter plates, solid supports, test tubes, trays and the like as well as antisera, for example in freeze dried form. The kit may also contain standard amounts of histamine whereby a standard curve may be constructed, containers for holding any necessary reagents for inducing an observable or otherwise measurable reaction and so on. Clearly, the skilled artisan can prepare a kit suitable for use in any particular immunoassay, the precise physical embodiment of which will depend upon the type assay contemplated.

A preferred test kit is similarly a mercantile unit prepared for determining induced histamine release from cells into biological fluids such as whole blood, basophils, urine, saliva and the like. The components of such a kit may include, for example, one or more agents for inducing histamine release, various diluents and buffers in addition to the antisera, microtiter plates, histamine standards, reagents and the like as described previously. This kit may also contain a histamine conjugate or antibody bound to a solid support as well as a labeled antibody or labeled conjugate of histamine.

The following examples are provided as a means of illustrating the present invention and are not to be construed as a limitation thereon.

EXAMPLE 1

Preparation of Histamine Propionic Acid Derivative

A solution of 1.11 grams (g) histamine (free base) and 3.02 milliliters (ml) of triethylamine in 10 ml of dimethylformamide (DMF) was added to a solution of 1.53 g of 3-bromo-propionic acid in 5 ml of DMF. This solution was stirred at room temperature for two hours and then heated at 80° C. for 2.5 hours after which time the solvents were removed by evaporation leaving a gummy residue. Said residue was dissolved in 10 ml of a buffer made of a mixture of $CHCl_3/MeOH/NH_4OH$ (10:5:1, respectively) and applied onto a 60 g silica gel column (packed in the same buffer). The column was eluted with this buffer at a rate of about 25 ml per fraction. The desired product was pooled (fractions 33–63) and evaporated to dryness. The residue was crystallized with 10 ml of ethanol to render 600 mg of the title compound (represented supra as formula X), melting point (m.p.) 190°–191° C.

Analysis calculated for $C_8H_{13}N_3O_2 \cdot \frac{1}{2}H_2O$:
C=49.99; H=7.34; N=21.87. Found:
C=50.62; H=7.51; N=21.89.

EXAMPLE 2

Preparation of Histamine Propionic Acid-Bovine Serum Albumin Immunogen Conjugate 68 mg of histamine propionic acid (prepared as described in Example 1) and bovine serum albumin (100 mg) were dissolved in 15 ml of $H_2O$. The resulting solution was cooled in an ice bath and the pH was adjusted to 4.5 with 1 normal (N) HCl. To this was added (with stirring) 320 mg of 1-ethyl-3-(3-dimethylaminopropyl)-carbodiimide hydrochloride (EDAC) in small portions. The pH of this reaction mixture was maintained at 4.5–5.0 (with 1N HCl) throughout the addition of the EDAC and the mixture was then stirred at 0° C. for three hours and then overnight at 5° C. The pH of the mixture was then adjusted to 7.0 by the addition of 1N NaOH and the mixture was then applied onto a P-10 column (2.5×40 centimeters, equilibrated with a 0.025 molar phosphate buffer, pH 7.0). The same phosphate buffer was then used to elute the column. The first UV absorption protein peak was collected and the protein concentration was determined by absorption at 280 nanometers (nm) i.e., $A_{280}$ nm=0.66 for a solution of mg/ml. The amount of histamine was determined by the residual free-$NH_2$ group on the immunogen using Habeeb's TNBS method. Using this procedure, about 80-90 percent of the bovine serum albumin was recovered. The molar ratio of histamine:bovine serum albumin was found to be between 13 and 21.

EXAMPLE 3

Preparation of Histamine Propionic Acid-Keyhole Limpet Hemocyanin Immunogen Conjugate Keyhole limpet hemocyanin (200 mg crude, commercially available from Cal-Biochem) was mixed with 4 ml of 50 mM carbonate buffer (pH 9.6) and was briefly vortexed and sonicated. The pH of the resulting suspension was adjusted to pH 9.6 with 2N NaOH and was then stirred at room temperature overnight. The mixture was then centrifuged at 10,000 rpm for 15 minutes after which the supernatant was recovered and the total protein concentration was determined by absorption at 280nm (20 microliters of the solution was diluted with 2.0 ml $H_2O$ and $A_{280}$ nm=1.66 was used for a solution of mg/ml; about 100 mg of protein was recovered). 82 mg of histamine propionic acid (prepared as described in Example 1) was added to the above supernatant and the pH was adjusted to pH 5.0 by the addition of 1N HCl. Water was then used to bring the total volume to 7.5 ml and the solution was cooled in an ice bath. 1-ethyl-3-(3-dimethylaminopropyl)-carbodiimide (155 mg) was added to the cooled solution with stirring and the pH was maintained at between 4.7–4.9 for two hours (0° C.). The pH of the solution was then adjusted to 5.5 and was then stirred at 5° C. overnight. The mixture was transferred to dialysis tubing (cut off limit 12,000–14,000 dalton) and was dialyzed against phosphate buffered saline (1 liter) at 5° C. After five changes (7 days), the suspension in the tubing was recovered, a small portion of which was centrifuged at 10,000 rpm for 15 minutes. The supernatant was used to determine the protein concentration by absorption at 280 nm, and the amount of histamine was determined by the residual free-$NH_2$ group on the immunogen by Habeeb's TNBS method. All of the materials were combined and diluted to about 50 ml with phosphate buffered saline to render the desired immunogen conjugate. The molar ratio of histamine: keyhole limpet hemocyanin was found to be between 83 and 116.

EXAMPLE 4

Preparation of Histamine-Bovine Serum Albumin Immunogen Conjugate 75 mg of bovine serum albumin (BSA), 38.4 mg of 1-ethyl-3-(3-dimethylaminopropyl)-carbodiimide and 184 mg of histamine were mixed in a 0.1 molar boric acid solution to a total volume of 4.0 ml (pH maintained at 4–5). After stirring overnight (room temperature) the mixture was dialyzed extensively against phosphate buffered saline. Absorbance at 280 nanometers (nm) was measured and protein concentrations were calculated. Histamine epitope density was determined by scintillation counting using a tritiated histamine tracer, two representative runs having epitope densities of 17 and 53. The conjugates from the two runs were combined and used as described in the assay procedure of Example 6.

EXAMPLE 5

Antibody Production

Following standard techniques, female BALB/C mice were immunized with histamine propionic acid-bovine serum albumin and/or histamine propionic acid-keyhole limpet hemocyanin immunogen conjugates (prepared as described in Examples 2 and 3, respectively) and bled periodically over an approximately 4 month period. Spleen cells from immunized mice were mixed with the nonsecreting myeloma cell line X63.Ag8 653 (publicly available from the The American Type Culture Collection having accession number CRL 1580) at a ratio of 2:1, respectively and fused with 50% polyethylene glycol (1,500 M.W.) in the presence of RPMI 1640 medium containing no fetal bovine serum. The resulting hybridomas were seeded into 96-well microtiter plates with mouse thymocytes as feeder cells. The base tissue culture medium was composed of 15% fetal bovine serum and RPMI 1640 containing hypoxanthine and thymidine. Hybrids were selected by the addition of aminopterin to the culture medium.

Anti-histamine activity in whole serum was detected by polyethylene glycol (PEG) precipitation. Ten microliters ($\mu$l) of $^3$H-histamine (New England Nuclear) containing 70,000-100,000 counts per minute (cpm) were incubated with either 100 $\mu$l mouse serum (1:10 dilution with phosphate-buffered saline) or 100 $\mu$l tissue culture supernatant for 2-3 hours at room temperature. In the case of tissue culture supernatants, 100 $\mu$l bovine gamma globulin (2 mg/ml) was added. Antibody was precipitated with 600 $\mu$l polyethylene glycol (PEG) 6000 (20% w/v). The pellet was washed twice with PEG (20%), resuspended in distilled water, and taken up in 3 ml of liquid scintillation counting fluid for scintillation counting.

Cultures of hybridoma cells positive by the PEG precipitation assay were expanded and cloned by a single cell selection technique. With the aid of an inverted microscope, single cells were drawn from a dilute cell suspension into an elongated Pasteur pipet. The single cell was then seeded into a microtiter well containing mouse thymocyte feeder cells.

Cloned hybridomas ($10^7$ cells/mouse) were expanded in ascites in pristane primed BALB/C mice. Antibody from ascites was purified by caprylic acid precipitation as follows. Two volumes acetate buffer (60 mM, pH 4) were mixed with one volume ascites and the pH adjusted to 4.8. Caprylic acid (0.74 ml/10 ml ascites) was added dropwise at room temperature and the resulting suspension stirred for 30 minutes. After centrifugation at 4,000 xg, the supernatant was collected and dialyzed extensively against phosphate buffered saline at 4° C. to obtain an Ig fraction. High performance liquid chromatography of the purified Ig fraction revealed a predominant peak at a molecular weight corresponding to mouse IgG. Subclass and isotype analysis using a Chemicon Mouse isotyping kit determined that each of the hybrids expanded were producing IgG$_1$. Antibody affinities were measured using the RIA inhibition assay of Mueller (*Methods in Enzymology*, 92 (1983), 589–601, Academic Press). This method involves the determination of the fraction of antibody solution required to bind a specified amount of $^3$H-histamine (determined by the PEG precipitation assay). Then, the amount of cold histamine needed to inhibit 50% of the tracer binding was determined. Affinity constants of approximately $2 \times 10^6$ M$^{-1}$ were determined for the clones selected. Significantly, the antibody produced by this methodology does not exhibit substantial cross-reactivity with histidine (metabolic precursor of histamine) or 1-methylhistamine thus making said antibody useful in a whole blood assay for histamine. The hybridoma producing said antibody has been deposited with The American Type Culture Collection and has been given accession number HB 8831.

EXAMPLE 6

Histamine Release Assay

The histamine-bovine serum albumin conjugate of Example 4 was added to 0.1 molar NaHCO$_3$, pH 9.6 to a concentration of 75 $\mu$g/ml. 50 $\mu$l aliquots of this solution were placed in the wells of a round bottom microtiter tray (referred to as a "coating plate"). A few of the wells were either left open or filled with 50 $\mu$l of bovine serum albumin (75 $\mu$g/ml) in the 0.1 molar NaHCO$_3$ buffer to serve as controls. A lid with 96 pegs (such as NUNC TSP® or Falcon FAST® lids) was then placed on the coating plate and incubated for about one hour at room temperature. The lid with pegs was then removed and washed with 400 ml of a mixture of 0.05 percent Tween 20 in distilled water. A second microtiter tray (referred to as the "release plate") was then prepared for the histamine release process as follows. A histamine standard curve was prepared by placing 5.5 $\mu$l of histamine standard solutions in successive duplicate wells. These standard solutions contained 10,000, 3333, 1111, 370, 123 and 41 nanomolar (nM) of histamine, respectively in distilled water or Tris ACM diluent (i.e., a buffer of 25 millimolar, mM Tris (pH 7.6); 0.2 molar NaCl; 5 mM KCl; 0.3 mg human serum albumin; 1 mM CaCl$_2$; and 0.5 mM MgCl$_2$). In the course of the assay the concentrations of the histamine dilutions were further diluted ten-fold. Stock allergen in 50 percent glycerol was diluted into seven serial ten-fold dilutions using Tris ACM or distilled water as diluent. Aliquots (5.5 $\mu$l) from each dilution (not including stock) were placed in successive duplicate wells of the release plate. This process was repeated for each desired allergen to be tested until the finished release plate had 5.5 $\mu$l of either histamine standards, allergen dilutions or Tris ACM buffer (for control wells) in all desired wells. The release plate was then ready for use.

Heparinized blood from a subject patient was obtained and mixed (1:1) with Tris ACM buffer (each plate required about 2.5 ml blood mixed with 2.5 ml of Tris ACM). A monoclonal anti-histamine antibody-horseradish peroxidase conjugate was prepared by the periodate borohydride coupling method described by Paul Nakane, in *Immunoassays: Clinical Laboratory Techniques for the 1980's*, (Nakamura, R. M., Dito, W. R., and Tucker, E. S., editors), Alan R. Liss, Inc., New York (1978). A small amount of this antibody-enzyme conjugate was added to the Tris ACM/blood mixture to produce the proper pre-determined conjugate concentration (about 0.5 μg/ml). Aliquots (50 μl/well) of this mixture were then placed in each well of the release plate and incubated for 15 minutes at 37° C. to allow histamine release. Then, the lid prepared as described above with 96 pegs was placed on the release plate such that each peg was introduced into a well. This configuration was then incubated at room temperature for 30 minutes, after which the lid with the pegs was removed and washed with two 400 ml portions of Tween 20/water as described above. This lid with the pegs was then placed into a third microtiter tray (referred to as the "chromagen plate") to which had been added 50 μl/well of the following solution: 0.8 mg/ml of 2,2'-azino-di-(3-ethyl-benzthiazolone)-6-sulfonic acid (i.e., ABTS); and 2 mM urea peroxide in 0.1M citrate buffer (pH 4.2). After a suitable incubation time (about 15 minutes at room temperature) the pegs were removed and the absorbencies (415 nM) of the contents of each well of the chromagen plate were determined using an ELISA reader. Alternatively, an assessment of histamine release can be made by visual inspection particularly where the pegs were first coated in the coating plate with a histamine-protein conjugate, preferably the histamine-bovine serum albumin conjugate prepared in accordance with Example 4. Actual concentrations of released histamine can be obtained from the standard curve (prepared as described above) and plotted against the dilution of allergen, if desired. From such plots judgments regarding a patient's sensitivity to an allergen can be made. Histamine release that occurs at very dilute allergen level may indicate a high sensitivity and vice versa.

The data shown in Table I were obtained by the above-described histamine release assay from a blood sample taken from a patient clinically known to be sensitive to Timothy grass extract. This blood sample was challenged with various dilutions of Timothy grass extract and the amount of histamine released was determined by reference to a histamine standard curve as described above.

TABLE I

Histamine Release Upon Exposure To Timothy Grass Extract

| Absorbance[a] | Relative Allergen Concentration[b] | Histamine Concentration[c] |
|---|---|---|
| 0.730 | $10^{-1}$ | 72 |
| 0.912 | $10^{-2}$ | 50 |
| 0.894 | $10^{-3}$ | 54 |
| 0.593 | $10^{-4}$ | 90 |
| 0.431 | $10^{-5}$ | 125 |
| 0.920 | $10^{-6}$ | 42 |
| 1.518 | $10^{-7}$ | 6 |
| 1.630 | 0 | 0 |

[a]Average absorbance for two trials at 415 nM of the contents of each well of the chromagen plate following incubation with pegs attached to the lid. Values shown are adjusted for background effects.
[b]Relative to a stock Timothy Grass Extract that is 1:20 (w/V) in 50% glycerol.
[c]Concentration expressed in nanomolarity

What is claimed is:

1. The immunogen conjugate represented by the formula:

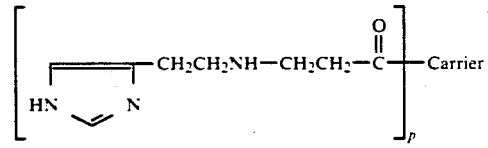

wherein p is from about 1 to about 120 and carrier is an immunogenic carrier material.

2. An antibody, capable of specifically binding with histamine prepared against a conjugate of claim 1.

3. A monoclonal antibody capable of specifically binding with histamine produced by a cell line having American Type Culture Collection accession number HB 8831.

4. The cell line having American Type Culture Collection accession number HB 8831.

5. In an immunoassay method for determining histamine, wherein the improvement comprises employing an antibody produced by a cell line having American Type Culture Collection accession number HB 8831.

6. A test kit for measuring histamine comprising the histamine immunogen conjugate of claim 1 bound to a solid support and a monoclonal antibody capable of specifically binding with histamine which antibody is produced by the cell line having American Type Culture Collection Accession Number HB 8831 and has been labeled with horseradish peroxidase.

* * * * *